US010306747B2

(12) United States Patent
Jin et al.

(10) Patent No.: US 10,306,747 B2
(45) Date of Patent: May 28, 2019

(54) CONTROLLING LINEAR ACCELERATOR

(71) Applicant: Shenyang Neusoft Medical Systems Co., Ltd., Shenyang (CN)

(72) Inventors: Feng Jin, Shenyang (CN); Peng Zhou, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 138 days.

(21) Appl. No.: 15/685,963

(22) Filed: Aug. 24, 2017

(65) Prior Publication Data
US 2018/0063939 A1  Mar. 1, 2018

(30) Foreign Application Priority Data
Aug. 26, 2016 (CN) .......................... 2016 1 0739790

(51) Int. Cl.
*H05H 7/22* (2006.01)
*A61N 5/10* (2006.01)
*H05H 9/00* (2006.01)

(52) U.S. Cl.
CPC ............. *H05H 7/22* (2013.01); *A61N 5/1048* (2013.01); *A61N 5/1081* (2013.01); *H05H 9/00* (2013.01)

(58) Field of Classification Search
None
See application file for complete search history.

(56) References Cited

U.S. PATENT DOCUMENTS

| 7,695,192 | B2 * | 4/2010 | Henderson | A61B 6/037 378/198 |
| 9,358,406 | B2 * | 6/2016 | Prieels | A61N 5/1048 |
| 9,623,263 | B2 * | 4/2017 | Cheng | A61N 5/107 |
| 10,154,822 | B2 * | 12/2018 | Henderson | A61B 6/0457 |
| 2003/0201403 | A1 * | 10/2003 | Svatos | A61N 5/1049 250/505.1 |
| 2008/0267352 | A1 * | 10/2008 | Aoi | A61N 5/10 378/65 |

(Continued)

FOREIGN PATENT DOCUMENTS

| CN | 202263308 U | * | 6/2012 |
| CN | 202263308 U |   | 6/2012 |

(Continued)

OTHER PUBLICATIONS

State Intellectual Property Office of the People's Republic of China, Office Action and Search Report Issued in Application No. 201610739790.4, dated Jul. 13, 2018, 11 pages. (Submitted with Partial Translation).

*Primary Examiner* — Andrew Smyth
(74) *Attorney, Agent, or Firm* — McCoy Russell LLP

(57) ABSTRACT

A method and device for controlling a linear accelerator as well as a linear accelerating system are provided according to examples of the present disclosure. In an example, a first component of the linear accelerator is controlled to move according to a motion instruction; when it is detected that the first component reaches a first position, the first component is controlled to pause moving, and a second component of the linear accelerator is controlled to move in a preset direction; when it is detected that the second component reaches a second position, the second component is controlled to stop moving, and the first component is controlled to continue to move according to the motion instruction.

19 Claims, 5 Drawing Sheets

(56) References Cited

U.S. PATENT DOCUMENTS

| | | | | |
|---|---|---|---|---|
| 2011/0121197 A1* | 5/2011 | Maeda | ................ | A61B 6/0457 |
| | | | | 250/453.11 |
| 2013/0150646 A1* | 6/2013 | Scholz | ................ | A61N 5/1031 |
| | | | | 600/1 |
| 2013/0317343 A1* | 11/2013 | Klimenko | .............. | A61B 5/055 |
| | | | | 600/411 |
| 2017/0087389 A1* | 3/2017 | Benner | ................ | A61N 5/1082 |

FOREIGN PATENT DOCUMENTS

| | | | | | |
|---|---|---|---|---|---|
| CN | 105311755 | A | * | 2/2016 | |
| CN | 105311755 | A | | 2/2016 | |
| CN | 205235194 | U | * | 5/2016 | |
| CN | 205235194 | U | | 5/2016 | |
| CN | 105920739 | A | * | 9/2016 | |
| CN | 105920739 | A | | 9/2016 | |
| CN | 105311755 | B | * | 5/2018 | |
| CN | 105920739 | B | * | 5/2018 | |
| WO | 2016116868 | A1 | | 7/2016 | |
| WO | WO-2016116868 | A1 | * | 7/2016 | ............. A61N 5/103 |

\* cited by examiner

CONTROLLING LINEAR ACCELERATOR

CROSS REFERENCE TO RELATED APPLICATIONS

This application claims priority to Chinese Patent Application No. 201610739790.4 entitled "Method and Apparatus for Controlling Linear Accelerator" which is filed on Aug. 26, 2016, the entire content of which is incorporated herein by reference for all purposes.

TECHNICAL FIELD

The present disclosure relates to controlling a linear accelerator.

A linear accelerator can be used in radioactive therapy for tumors. The linear accelerator may include components such as a gantry, a turntable, and a treatment bed. A treatment head may be arranged on the gantry. The turntable may have a mechanical connection with the treatment bed. When the linear accelerator is used, the gantry can rotate around the treatment bed in a vertical direction, and the turntable can rotate in a horizontal direction and drive the treatment bed to move simultaneously.

BACKGROUND

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

To provide a better understanding of the technical solutions of the present disclosure to those skilled in the art, the technical solutions of embodiments of the present disclosure will be described clearly and fully below in combination with drawings in the embodiments of the present disclosure. It is apparent that the described embodiments are merely part of embodiments of the present disclosure rather than all embodiments. Other embodiments achieved by those of ordinary skill in the art based on the embodiments in the present disclosure without paying creative work shall all fall into the scope of protection of the present disclosure.

In a linear accelerator, when a component moves, the moving component may collide with another component. For example, a rotating gantry may collide with a treatment bed. Thus, it may cause damage for equipment or cause injury for a patient in a way that safety is relatively low. How to effectively prevent a collision when a component of the linear accelerator moves becomes a problem to be solved at present.

Figure 1:
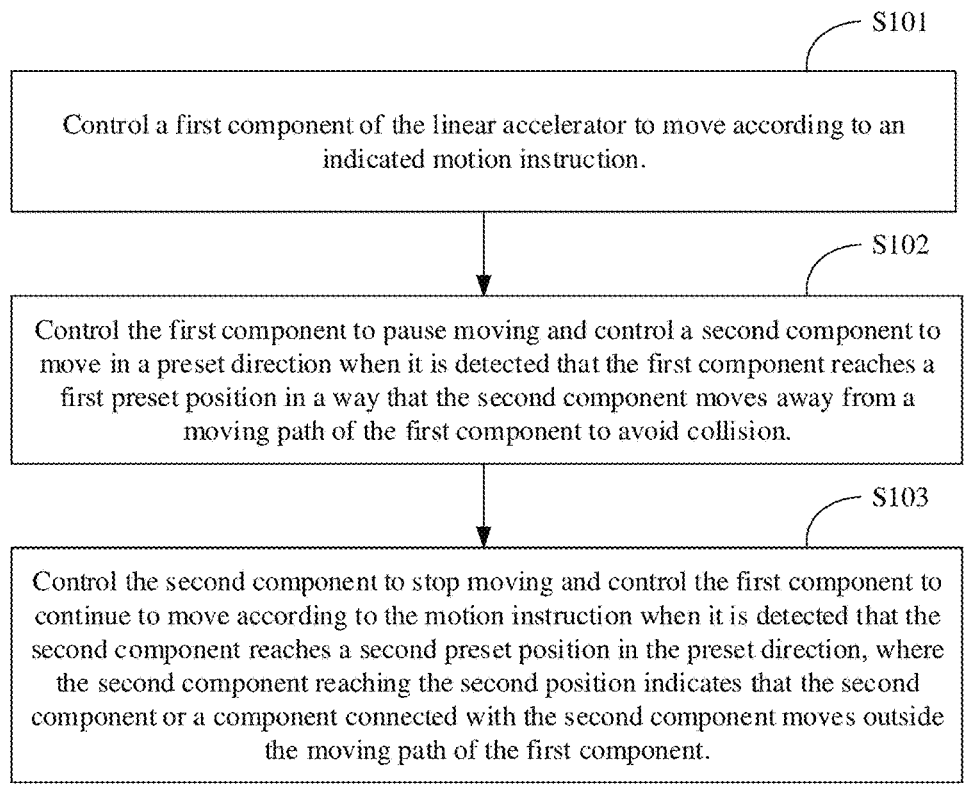
FIG. 1 is a flowchart illustrating a method of controlling a linear accelerator according to an example of the present disclosure.

Referring to FIG. 1, a method of controlling a linear accelerator is provided according to an example of the present disclosure.

Figure 2:
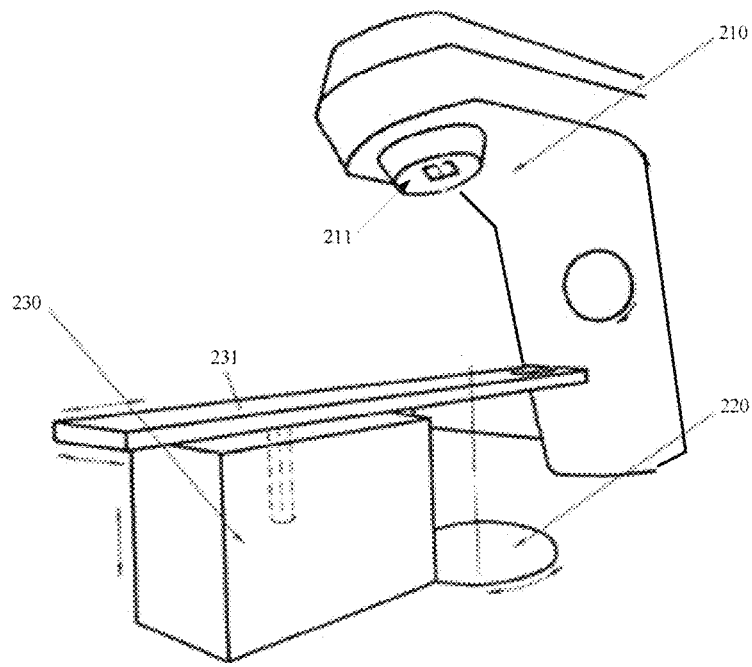
FIG. 2 is a schematic diagram illustrating a structure of a linear accelerator according to an example of the present disclosure.
Figure 3:
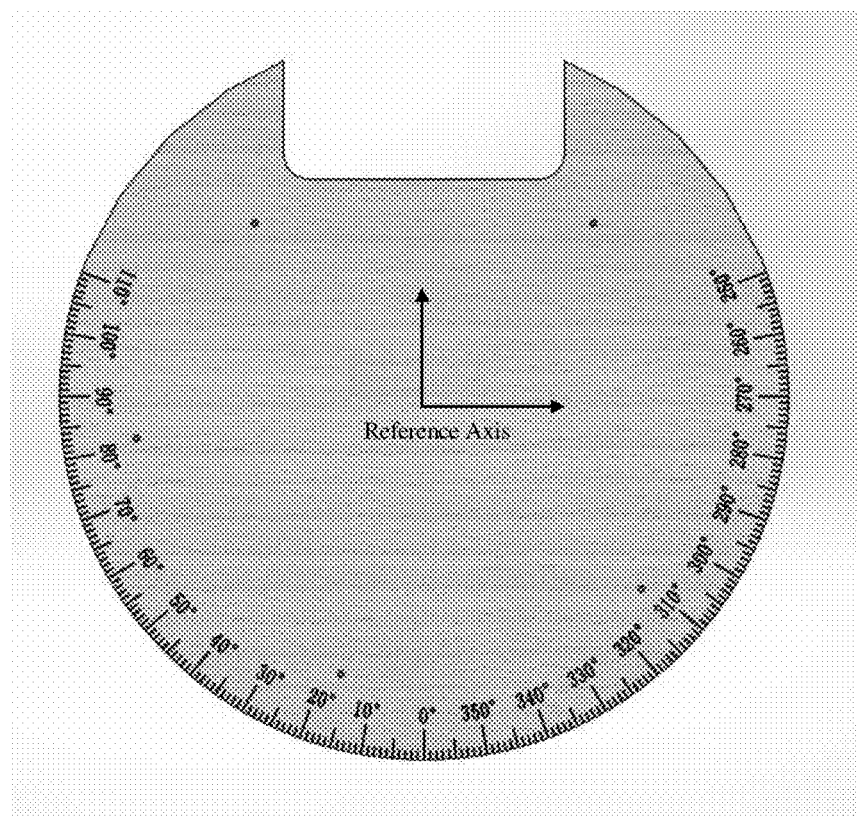
FIG. 3 is a schematic illustration of a graduated scale according to an example of the present disclosure.

As shown in FIG. 2, the linear accelerator in the example includes a gantry 210, a turntable 220 and a treatment bed 230. A treatment head 211 is arranged on the gantry 210. The turntable 220 has a mechanical connection with the treatment bed 230. The gantry 210 of the linear accelerator may rotate around the treatment bed 230 in a vertical direction. The turntable 220 may rotate in a horizontal direction. When rotating in the horizontal direction, the turntable 220 can simultaneously drive the treatment bed 230 to move. Further, a vertical motor and a graduated scale, shown in FIG. 3, may be arranged on the turntable 220. The graduated scale may be arranged on an upper surface of the turntable 220 to facilitate observation, and the vertical motor may control the graduated scale to perform vertical motion in a vertical direction.

In the example, the control method includes procedures as follow.

At block S101, a first component of the linear accelerator is controlled to move according to an indicated motion instruction.

The first component may be the gantry 210 or the turntable 220. For example, when a motion instruction from a user is received, according to the motion instruction, the gantry 210 is controlled to rotate in a vertical direction, or the turntable 220 is controlled to rotate in a horizontal direction, or the graduated scale on the turntable 220 is controlled to ascend or descend in a vertical direction.

At block S102, when it is detected that the first component reaches a first preset position, is controlled to pause moving, and a second component is controlled to move in a preset direction in a way that the second component moves away from a moving path of the first component to avoid collision.

When the first component is the gantry 210, the second component is the turntable 220. When the first component is the turntable 220, the second component is the gantry 210.

The first component reaching the first preset position indicates that the first component may collide with the second component or a component connected with the second component when continuing to move. For example, the second component or the component connected with the second component is on the moving path of the first component. To avoid collision, even though receiving the motion instruction, the linear accelerator may control the first component to pause moving and control the second component to move in a direction away from the moving path of the first component. In an example of the present disclosure, the moving path is a future moving path indicated by the motion instruction.

For example, the gantry 210 rotating to the first preset position in the vertical direction indicates that the gantry 210 may collide with the turntable 220 or the treatment bed 230 when continuing to rotate. The gantry 210 may be controlled to pause rotating, and the turntable 220 is controlled to move in a direction away from the moving path of the gantry 210. For example, the turntable 220 may be controlled to rotate to an initial position in the horizontal direction (a rotating angle is 0 degree). When a graduated scale is arranged on the turntable 22, the graduated scale may further be controlled to descend below a designated height (e.g., a height of 40 cm) in the vertical direction.

At block S103, when it is detected that the second component reaches a second preset position in the preset direction, the second component is controlled to stop moving, and the first component is controlled to continue to move according to the motion instruction, where the second component reaching the second position indicates that the second component or a component connected with the second component moves outside the moving path of the first component.

The second component reaching the second preset position in the preset direction indicates that the second component and the component connected with the second component moves outside the moving path of the first component. In this case, when the first component continues to move, the first component cannot collide with the second component or the component connected with the second component. Thus, the second component may be controlled to stop moving, and the first component may be controlled to continue to move according to the motion instruction.

The second component is controlled to move toward an initial angle of the second component. In an example, the process of controlling the second component to move in the preset direction may include: controlling the second component to move toward the initial angle of the second component. The process of detecting that the second component reaches the second preset position in the preset direction may at least include detecting that the second component reaches the initial angle of the second component. For example, when it is detected that the turntable 220 reaches the second preset position in the preset direction, the turntable 220 rotates to the initial position (0 degree) in the horizontal direction in a way that the gantry 210 cannot collide with the turntable 220 or the treatment bed 230 even though the gantry 210 continues to move. Thus, the turntable 220 is controlled to stop moving, and the gantry 210 is controlled to continue to rotate in the vertical direction according to a motion instruction.

When a graduated scale is arranged on the turntable 220, the graduated scale may further be controlled to descend below a height threshold (e.g., 40 cm) in the vertical direction when the turntable 220 rotates to the initial position in the horizontal direction, where the height threshold may be decided based on a height of the moving path of the gantry 210. For example, the height threshold may be less than the height of the moving path of the gantry 210. Thus, when the graduated scale descends below the height threshold, the gantry 210 does not collide with the graduated scale when the gantry continues to rotate along the moving path.

In the example, the control method may be executed by a controller (e.g., a motor motion controlling board) on a linear accelerator, or may be executed by a host computer corresponding to the linear accelerator, or may be executed by the controller and the host computer together, which is not limited in the present disclosure.

When the method is executed by the controller and the host computer together, the controller may feed detection results of components such as the gantry and the turntable back to the host computer. The host computer may instruct the controller to control a corresponding component according to a received detection result. For example, at block S102, when it is detected that the first component reaches the first preset position, the controller transmits a feedback signal to the host computer, where the feedback signal indicates that the first component reaches the first preset position. When receiving the feedback signal, the host computer transmits a motion instruction to the controller on the linear accelerator, where the motion instruction instructs the controller to control the first component to pause moving and control the second component to move in the preset direction. When receiving the motion instruction, the controller may control the first component to pause moving and control the second component to move in the preset direction according to the motion instruction.

It can be seen from the technical solution above, in examples of the present disclosure, when the first component of the linear accelerator is controlled to move according to the indicated motion instruction, the first component is controlled to pause moving, and the second component is controlled to move in the preset direction when it is detected that the first component reaches the first preset position, so that the second component moves away from the moving path of the first component to avoid collision, where the first component reaching the first preset position indicates that the first component may collide with the second component or a component connected with the second component when the first component continues to move. When it is detected that the second component reaches the second preset position in the preset direction, the second component is controlled to stop moving and the first component is controlled to continue to move according to the motion instruction, where the second component reaching the second preset position indicates that the second component and the component connected with the second component moves outside the moving path of the first component. Thus, according to examples of the present disclosure, when the first component of the linear accelerator is controlled to move, the second component can be automatically move away from the moving path of the first component according to arrival positions of the first component, thereby effectively avoiding collision between components. For example, as shown in FIG. 2, a collision between the gantry 210 and the turntable 220 or a collision between the gantry 210 and the treatment bed 230 can be avoided, thereby improving the safety.

In an example, before the first component is controlled to move according to a first motion instruction instructed, the second component may further be controlled to move according to a second motion instruction instructed. Thus, when a plurality of components of the linear accelerator move simultaneously, e.g., the gantry 210 and the turntable 220 simultaneously move, a collision between the components can be effectively avoided, thereby improving the safety.

In an example, the turntable 220 may rotate in the horizontal direction, and the graduated scale on the turntable 220 may perform vertical motion in the vertical direction. When different components of the linear accelerator perform complex motion together, e.g., the gantry 210 rotates in the vertical direction (which may respectively rotate clockwise and counterclockwise by 180 degrees), the turntable 220 rotates in the horizontal direction, and the graduated scale performs the vertical motion in the vertical direction, the linear accelerator can control the components not to collide with each other.

In an example, when the first component reaches the first preset position, it is determined whether the second component reaches the second preset position. If yes, the first component is controlled to continue to move rather than to pause. If no, execute the block S102.

In an example of the present disclosure, whether a preset position is reached may be determined by detecting an angle and/or a height, which will be described in detail below.

When the first component is the gantry 210 and the second component is the turntable 220, the process of detecting that the first component reaches the first preset position may include detecting that a rotating angle of the gantry 210 reaches a first preset angle. And the process of detecting that the second component reaches the second preset position in the preset direction may include detecting that a rotating angle of the turntable 220 reaches a second preset angle. Further, when a graduated scale is arranged on the turntable 220, the process of detecting that the second component reaches the second position in the preset direction may further include detecting that an ascending-descending height of the graduated scale on the turntable 220 reaches a first preset height.

When the first component is the turntable 220 and the second component is the gantry 210, the process of detecting that the first component reaches the first preset position may include detecting that a rotating angle of the turntable 220 reaches a third preset angle. And the process of detecting that the second component reaches the second preset position in the preset direction may include detecting that a rotating angle of the gantry 210 reaches a fourth preset angle. Further, when a graduated scale is arranged on the turntable 220, the process of detecting that the first component reaches the first preset position may further include detecting that a vertical height of the graduated scale on the turntable 220 reaches a second preset height.

In an example of the present disclosure, the rotating angle of the gantry 210, the rotating angle of the turntable 220 and the vertical height may be detected by detecting modules such as encoders, detection boards and limit switches. Specifically, a first detecting module may be arranged on the gantry 210, which is configured to detect the rotating angle of the gantry 210; a second detecting module is arranged on the turntable 220, which is configured to detect the rotating angle of the turntable 220; a third detecting module may be further arranged on the turntable 220 when a graduated scale is arranged on the turntable 220, which is configured to detect the vertical height of the graduated scale on the turntable 220.

The first detecting module, the second detecting module, and the third detecting module are described below, respectively.

In an example, the first detecting module on the gantry 210 may include one or more detecting sub-modules as follows: an angle detecting board, an encoder and a limit switch.

The angle detecting board is a circuit board which may be configured to detect a rotating angle. The circuit board may include an angle sensor.

The encoder may be a photoelectric encoder which is configured to convert a mechanical geometric displacement into a pulse or digital signal through photoelectric conversion, so as to implement angle detection. The photoelectric encoder may include a raster disk and a photoelectric detecting apparatus. The raster disk may be a circular plate with a designated diameter. A plurality of rectangular through-holes may be evenly formed on the raster disk. When a motor rotates, the raster disk rotates at a same speed as the motor, and the photoelectric detecting apparatus including electronic elements such as light-emitting diodes may detect output pulse signals. A rotating angle is calculated according to the number of the output pulse signals.

The limit switch may be an electrical limit switch or a mechanical limit switch. A limit switch corresponding to a designated rotating angle may be arranged. Thus, when the gantry 210 rotates to the designated angle, the limit switch is triggered, so as to implement angle detection.

In an example of the present disclosure, the rotating angle of the gantry 210 may be detected by a plurality of detecting sub-modules. When a difference between the angles respectively detected by the detecting sub-modules is large, the gantry 210 may be controlled to stop moving, so as to implement safety protection for the linear accelerator. For example, the first detecting module may include a first angle detecting board and a first encoder. The control method may further include: controlling the gantry 210 to stop moving when a difference between an angle detected by the first angle detecting board and an angle detected by the first encoder reaches a first preset difference value. In particular, the angle detected by the first detecting board and the angle detected by the first encoder may be compared in real time.

In an example, the second detecting module on the turntable 220 may include one or more detecting sub-modules as follows: an angle detecting board, an encoder and a limit switch.

In an example, the rotating angle of the turntable 220 may be detected by a plurality of detecting sub-modules. When a difference between the angles respectively detected by the detecting sub-modules is large, the turntable 220 may be controlled to stop moving, so as to implement safety protection for the linear accelerator. For example, the second detecting module may include a second angle detecting board and a second encoder. The control method may further include: controlling the turntable 220 to stop moving when a difference between an angle detected by the second angle detecting board and an angle detected by the second encoder reaches a second preset difference value, where the angle detected by the second detecting board and the angle detected by the second encoder may be compared in real time.

In an example, the first detecting module for the graduated scale on the turntable 220 may include one or more detecting sub-modules as follows: a height detecting board, an encoder and a limit switch.

The height detecting board may be a circuit board configured to detect a vertical height. The circuit board may include a height sensor.

The encoder may be a photoelectric encoder which is configured to convert a mechanical geometric displacement into a pulse or digital signal through photoelectric conversion, so as to implement height detection.

The limit switch may be an electrical limit switch or a mechanical limit switch. A limit switch corresponding to a designated vertical height may be arranged. For example, when the graduated scale ascends or descends to the designated height, the limit switch is triggered, so as to implement detection for the vertical height.

In an example of the present disclosure, the vertical height of the graduated scale on the turntable 220 may be detected by a plurality of detecting sub-modules. When a difference between heights respectively detected by the detecting sub-modules is large, the linear accelerator controls the graduated scale to stop moving, so as to implement safety protection for the linear accelerator. For example, the third detecting module may include a height detecting board and a third encoder. The control method may further include: controlling the graduated scale on the turntable 220 to stop moving when a difference between a height detected by the height detecting board and a height detected by the third encoder reaches a third preset difference value. The height detected by the height detecting board and the height detected by the third encoder may be compared in real time.

In an example, limit switches may be used to determine whether the gantry 210 and the turntable 220 respectively reach the first preset position and the second preset position. The limit switches may further be configured to limit maximum moving ranges of the gantry 210 and the turntable 220, so as to prevent the rotating angle of the gantry 210 as well as the rotating angle and the vertical height of the turntable 220 exceed safety ranges. Detailed descriptions are made below.

In an example, a first limit switch may further be arranged on the gantry 210. The first limit switch may be arranged at a position corresponding to a maximum rotating limit (i.e., corresponding to a maximum rotating motion limit) on the gantry 210, e.g., a position where the rotating angle is 0 degree, a position where the rotating angle is 180 degrees. Accordingly, the control method may further include: when it is detected that the first limiting switch is triggered, controlling the gantry 210 to stop moving when determining that the gantry 210 rotates to a limit.

In an example, a second limit switch may be arranged on the turntable 220. The second limit switch may be arranged at a position corresponding to a maximum rotating limit on the turntable 220, e.g., a position where the rotating angle is 0 degree, a position where the rotating angle is 90 degrees. Accordingly, the control method may further include: when it is detected that the second limit switch is triggered, controlling the turntable 220 to stop moving when determining that the turntable 220 rotates to a limit.

In an example, when a graduated scale is arranged on the turntable 220, a third limit switch may further be arranged on the turntable 220, which may be arranged at a position corresponding to a maximum vertical limit (including an ascending limit and/or a descending limit) for the graduated scale. Accordingly, the control method may further include: when detecting the third limit switch is triggered, which indicates that a height of the graduated scale reaches the ascending limit or the descending limit, controlling the graduated scale to stop moving.

An exemplary example of the present disclosure is provided below.

Figure 4:
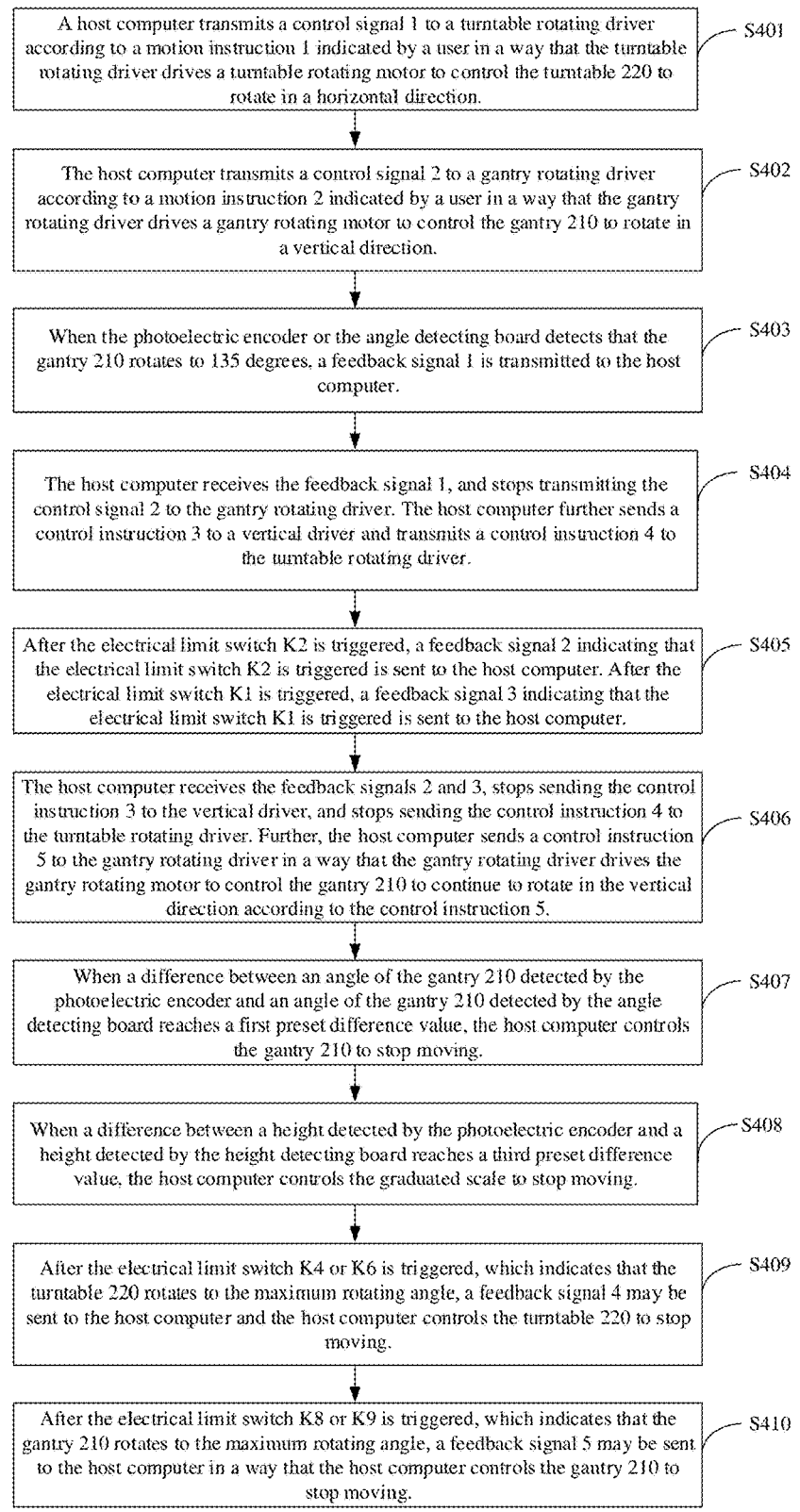
FIG. 4 is a schematic flowchart illustrating a method according to an example of the present disclosure.

FIG. 4 illustrates a method of controlling a linear accelerator according to an example of the present disclosure.

As shown in FIG. 2, the linear accelerator in the example includes the gantry 210, the turntable 220 and the treatment bed 230.

A treatment head 211, a photoelectric encoder, an angle detecting board, an electrical limit switch and an electrical limit switch may be arranged on the gantry 210. A gantry rotating motor on the gantry 210 may be driven though a gantry rotating driver, so as to drive the gantry 210 to rotate around the treatment bed 230 in a vertical direction. The photoelectric encoder and the angle detecting board may be configured to detect a rotating angle of the gantry 210 in real time. An electrical limit switch K8 and an electrical limit switch K9 may be configured to limit a maximum rotating range of the gantry 210 clockwise and counterclockwise, respectively. For example, the gantry 210 may be limited to rotate clockwise and counterclockwise maximally to 180 degrees, thereby preventing the gantry 210 from rotating excessively.

A photoelectric encoder, an electrical limit switch K1, an electrical limit switch K4, an electrical limit switch K6, a mechanical limit switch K5 and a mechanical limit switch K7 may be arranged on the turntable 220. The photoelectric encoder is used to detect a rotating angle of the turntable 220. An initial angle of the turntable may be 0 degrees. The electrical limit switch K1 may be configured to limit the turntable 220 maximally to rotate back to 0 degrees when beginning to rotate from the initial angle. The electrical limit switch K4 and the mechanical limit switch K5 may be configured to limit a maximum rotating angle of the turntable 220 in a clockwise direction, e.g., to limit that the turntable 220 rotates clockwise maximally to 90 degrees. The electrical limit switch K6 and the mechanical limit switch K7 may be configured to limit a maximum rotating angle of the turntable 220 in a counterclockwise direction, e.g., to limit that the turntable 220 rotates counterclockwise maximally to 90 degrees.

A graduated scale may be arranged on an upper surface of the turntable 220. A photoelectric encoder, a height detecting board, an electrical limit switch K2 and an electrical limit switch K3 may be further arranged on the turntable 220. The photoelectric encoder and the height detecting board may be configured to detect a vertical height of the graduated scale. The electrical limit switch K2 may be configured to detect whether the graduated scale descends to a position corresponding to a first height (e.g., a height of 40 cm). The electrical limit switch K3 may be configured to detect whether the graduated scale ascends to a position corresponding to a second height, where the second height is larger than the first height.

The turntable 220 may have a mechanical connection with the treatment bed 230. A turntable rotating motor on the turntable 220 may driven by a turntable rotating driver, so as to drive the turntable 220 to rotate in a horizontal direction, and accordingly to drive the treatment bed 230 to move. The treatment bed 230 may further be driven to perform vertical motion in the vertical direction. A vertical motor arranged on the turntable 220 may be driven through a vertical driver, so as to control the graduated scale to perform the vertical motion in the vertical direction.

Figure 5:
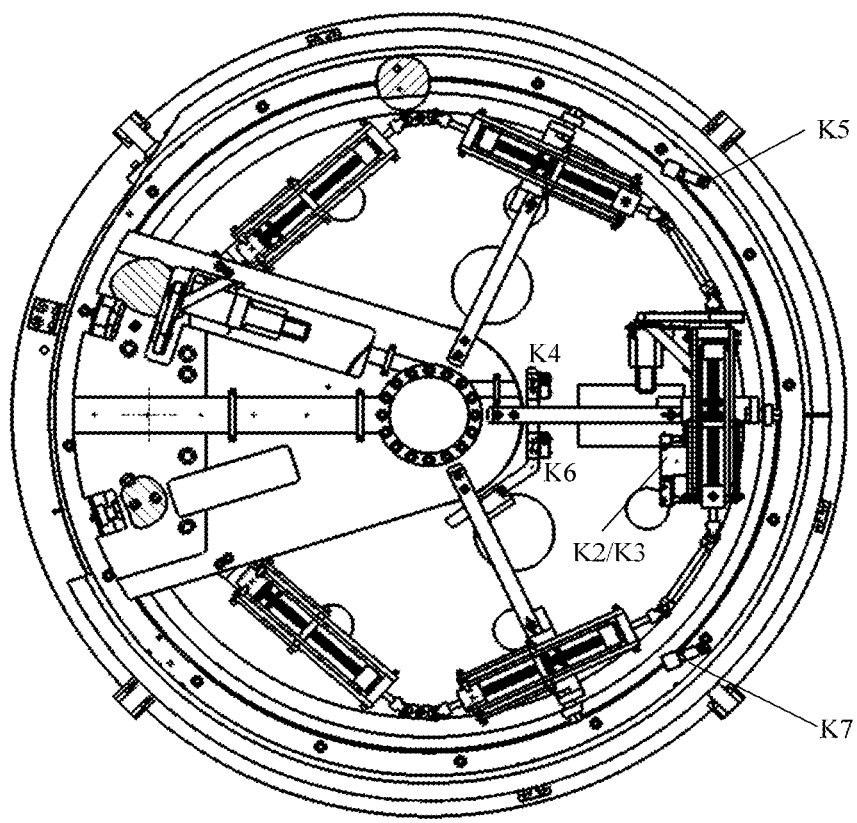
FIG. 5 is a schematic diagram illustrating a structure of a turntable according to an example of the present disclosure.

The positions of the electrical limit switch K4, the electrical limit switch K6, the mechanical limit switch K5, the mechanical limit switch K7, the electrical limit switch K2, and the electrical limit switch K3 arranged on the turntable 220 are shown in FIG. 5.

As shown in FIGS. 2 and 4, in the example, the control method includes procedures as follow.

At block S401, a host computer transmits a control signal 1 to a turntable rotating driver according to a motion instruction 1 indicated by a user in a way that the turntable rotating driver drives a turntable rotating motor to control the turntable 220 to rotate in a horizontal direction.

At block S402, the host computer transmits a control signal 2 to a gantry rotating driver according to a motion instruction 2 indicated by a user in a way that the gantry rotating driver drives a gantry rotating motor to control the gantry 210 to rotate in a vertical direction.

At block S403, when the photoelectric encoder or the angle detecting board detects that the gantry 210 rotates to 135 degrees, a feedback signal 1 is transmitted to the host computer.

At block S404, the host computer receives the feedback signal 1, and stops transmitting the control signal 2 to the gantry rotating driver in a way that the gantry rotating driver stops driving the gantry rotating motor, and the gantry 210 pauses to move accordingly. Further, the host computer transmits a control instruction 3 to a vertical driver and sends a control instruction 4 to the turntable rotating driver in a way that the vertical driver drives the vertical motor to control the graduated scale to perform descending motion according to the control instruction 3, and the turntable rotating driver drives the turntable rotating motor to control the turntable 220 to rotate toward an initial angle (e.g., 0 degree) according to the control instruction 4.

At block S405, after the electrical limit switch K2 is triggered, which indicates that the graduated scale descends to a position corresponding to the first height (e.g., 40 cm), a feedback signal 2 indicating that the electrical limit switch K2 is triggered is sent to the host computer. After the electrical limit switch K1 is triggered, which indicates that the turntable 220 rotates back to the initial angle (e.g., 0 degree), a feedback signal 3 indicating that the electrical limit switch K1 is triggered is sent to the host computer.

At block S406, the host computer receives the feedback signals 2 and 3, stops sending the control instruction 3 to the vertical driver, and stops sending the control instruction 4 to the turntable rotating driver, so that the vertical driver stops driving the vertical motor in a way that the graduated scale stops descending, and the turntable rotating driver stops driving the turntable rotating motor in a way that the turntable 220 stops rotating. Further, the host computer sends a control instruction 5 to the gantry rotating driver in a way that the gantry rotating driver drives the gantry rotating motor to control the gantry 210 to continue to rotate in the vertical direction according to the control instruction 5.

In an example, the control method may further include procedures as follow.

At block S407, when a difference between an angle of the gantry 210 detected by the photoelectric encoder and an angle of the gantry 210 detected by the angle detecting board reaches a first preset difference value, the host computer controls the gantry 210 to stop moving.

At block S408, when a different between a height detected by the photoelectric encoder and a height detected by the height detecting board reaches a third preset difference value, the host computer controls the graduated scale to stop moving.

At block S409, after the electrical limit switch K4 or K6 is triggered, which indicates that the turntable 220 rotates to the maximum rotating angle, a feedback signal 4 may be sent to the host computer in a way that the host computer controls the turntable 220 to stop moving.

At block S410, after the electrical limit switch K8 or K9 is triggered, which indicates that the gantry 210 rotates to the maximum rotating angle, a feedback signal 5 may be sent to the host computer in a way that the host computer controls the gantry 210 to stop moving.

Corresponding to the method examples above, the present disclosure further provides examples for a control device, which will be described in detail below.

Figure 6:
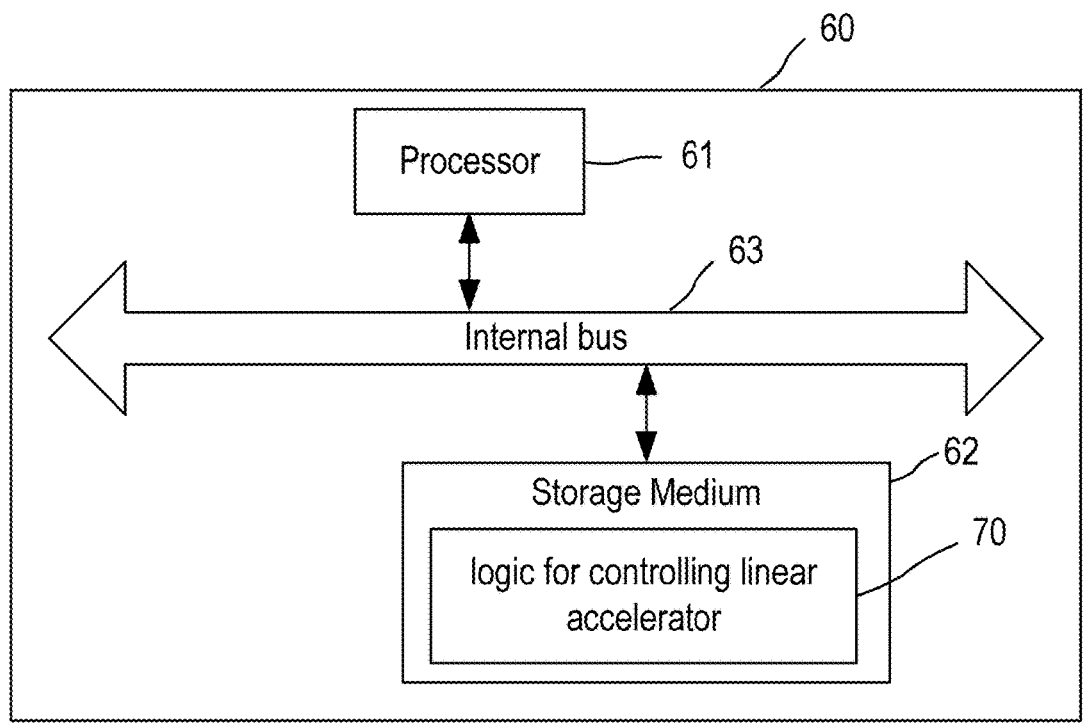
FIG. 6 is a schematic diagram of a hardware structure of an apparatus for controlling a linear accelerator according to an example of the present disclosure.

FIG. 6 is a schematic diagram illustrating a hardware structure of a device for controlling a linear accelerator according to one and more examples of the present disclosure. A device 60 may include a processor 61 and a machine-readable storage medium 62. The processor 61 and the machine readable storage medium 62 may communicate with each other via a system bus 63. Further, the processor 61 may execute the method of controlling a linear accelerator described above by reading and executing machine executable instructions corresponding to a logic 70 for controlling a linear accelerator and stored in the machine-readable storage medium 62.

As used herein, the machine-readable storage medium 62 may be any electronic, magnetic, optical, or other physical storage apparatus to contain or store information such as executable instructions, data, and the like. For example, any machine-readable storage medium described herein may be any of Random Access Memory (RAM), volatile memory, non-volatile memory, flash memory, a storage drive (e.g., a hard drive), a solid state drive, any type of storage disc (e.g., a compact disc, a DVD, etc.), and the like, or a combination thereof.

Figure 7:
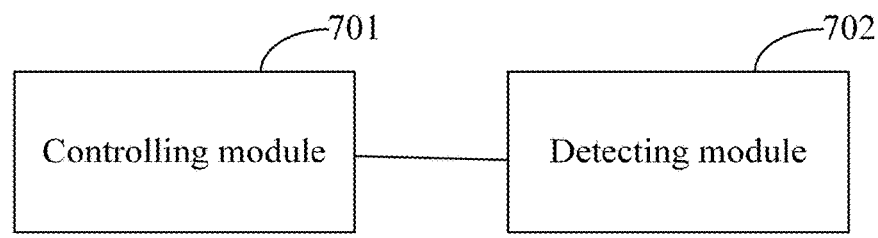
FIG. 7 is a schematic diagram illustrating a structure of logic for controlling a linear accelerator according to an example of the present disclosure.

FIG. 7 is a schematic diagram illustrating logic for controlling a linear accelerator according to an example of the present disclosure.

As shown in FIG. 2, the linear accelerator in the example includes a gantry 210, a turntable 220 and a treatment bed 230. A treatment head 211 is arranged on the gantry 210. The turntable 220 has a mechanical connection with the treatment bed 230. The gantry 210 of the linear accelerator may rotate around the treatment bed 230 in a vertical direction. The turntable 220 may rotate in a horizontal direction. When rotating in the horizontal direction, the turntable 220 can simultaneously drive the treatment bed 230 to move. Further, a vertical motor and a graduated scale shown in FIG. 3 may be arranged on the turntable 220. The graduated scale may be arranged on an upper surface of the turntable 220 to facilitate observation, and the vertical motor may control the graduated scale to perform vertical motion in a vertical direction.

In this example, the control device 70 includes: a controlling module 701 and a detecting module 702.

The controlling module 701 is configured to control a first component of the linear accelerator to move according to a motion instruction.

The first component may be the gantry 210 or the turntable 220. For example, when a motion instruction from a user is received, according to the motion instruction, the gantry 210 is controlled to rotate in a vertical direction, or the turntable 220 is controlled to rotate in a horizontal direction, or the graduated scale on the turntable 220 is controlled to ascend or descend in a vertical direction.

The detecting module 702 is configured to when it is detected that the first component reaches a first position, control the first component to pause moving and controlling a second component of the linear accelerator to move in a preset direction in a way that the second component moves away from a moving path of the first component.

When the first component is the gantry 210, the second component is the turntable 220. When the first component is the turntable 220, the second component is the gantry 210.

The first component reaching the first preset position indicates that the first component may collide with the second component or a component connected with the second component when continuing to move. For example, the second component or the component connected with the second component is on the moving path of the first component. To avoid collision, even though receiving the motion instruction, the linear accelerator may control the first component to pause moving and control the second component to move in a direction away from the moving path of the first component. In an example of the present disclosure, the moving path is a future moving path indicated by the motion instruction.

The detecting module 702 is configured to when it is detected that the second component reaches a second position, control the second component to stop moving and controlling the first component to continue to move according to the motion instruction, wherein the second component reaching the second position indicates that the second component or a component connected with the second component moves outside the moving path of the first component.

The second component reaching the second preset position in the preset direction indicates that the second component and the component connected with the second component moves outside the moving path of the first component. In this case, when the first component continues to move, the first component cannot collide with the second component or the component connected with the second component. Thus, the second component may be controlled to stop moving, and the first component may be controlled to continue to move according to the motion instruction.

In an example, the second component is controlled to move toward an initial angle of the second component. For example, when controlling the second component to move in the preset direction, the controlling module 701 is configured to control the second component to move toward the initial angle of the second component. When detecting the second component reaches the second preset position in the preset direction, the detecting module 702 is configured to detect the second component reaches the initial angle of the second component.

In an example of the present disclosure, the controlling module 701 is further configured to before the first component is controlled to move according to a first motion instruction instructed, control the second component to move according to a second motion instruction instructed. Thus, when a plurality of components of the linear accelerator move simultaneously (e.g., the gantry 210 and the turntable 220 simultaneously move), a collision between the components can be effectively avoided, thereby improving the safety. In an example, the turntable 220 may rotate in the horizontal direction, and the graduated scale on the turntable 220 may perform vertical motion in the vertical direction. When different components of the linear accelerator perform complex motion together (e.g., the gantry 210 rotates in the vertical direction (which may respectively rotate clockwise and counterclockwise by 180 degrees), the turntable 220 rotates in the horizontal direction, and the graduated scale performs the vertical motion in the vertical direction), the linear accelerator can control the components not to collide with each other.

In an example of the present disclosure, whether a preset position is reached may be determined by detecting an angle and/or a height, which will be described in detail below.

The first component is the gantry 210 and the second component is the turntable 220. In this case, when detecting the first component reaches the preset position, the detecting module 702 is configured to detect that a rotating angle of the gantry 210 reaches a first preset angle. When detecting the second component reaches the second position in the preset direction, the detecting module 702 is configured to detect that a rotating angle of the turntable 220 reaches a second preset angle. Further, when a graduated scale is arranged on the turntable 220, the detecting module 702 is configured to detect that a rotating angle of the turntable 220 reaches the second preset angle and a vertical height of the graduated scale on the turntable 220 reaches a first preset height when detecting that the second component reaches the second preset position in the preset direction.

The first component is the turntable 220 and the second component is the gantry 210. In this case, when detecting the first component reaches the preset position, the detecting module 702 is configured to detect that a rotating angle of the turntable 220 reaches a third preset angle. When detecting the second component reaches the second preset position in the preset direction, the detecting module 702 is configured to detect that a rotating angle of the gantry 210 reaches a fourth preset angle. Further, when a graduated scale is disposed on the turntable 220, the detecting module 702 is configured to detect that the rotating angle of the turntable 220 reaches the third preset angle and a vertical height of the graduated scale on the turntable 220 reaches a second preset height when detecting the first component reaches the preset position.

In an example of the present disclosure, the rotating angle of the gantry 210 as well as the rotating angle and the vertical height of the turntable 220 may be detected by detecting modules such as encoders, detecting boards, and limit switches. Specifically, the detecting module 702 includes a second detecting module, where the second detecting module is arranged on the gantry 210 and configured to detect the rotating angle of the gantry 210. The detecting module 702 further includes a third detecting module, where the third detecting module is arranged on the turntable 220 and configured to detect the rotating angle of the turntable 220. In an example, when a graduated scale is arranged on the turntable 220, the detecting module 702 may further include a first detecting module arranged on the turntable 220, where the first detecting module is configured to detect a vertical height of the graduated scale on the rotating disk. The first detecting module, the second detecting module, and the third detecting module are described below, respectively.

In an example, the second detecting module may include any one or more detecting sub-modules as follows: an angle detecting board, an encoder, and a limit switch. In an example of the present disclosure, the rotating angle of the gantry 210 may be detected by a plurality of detecting sub-modules. When a difference between detected angles is large, the gantry 210 is controlled to stop moving, so as to implement safety protection for the linear accelerator. For example, the second detecting module includes a first angle detecting board and a second encoder. The controlling module 701 may further be configured to control the gantry 210 to stop moving when a difference between an angle detected by the first angle detecting board and an angle detected by the second encoder reaches a second preset difference value. In an example, the angle detected by the first detecting board and the angle detected by the second encoder may be compared in real time.

In an example, the third detecting module includes any one or more detecting sub-modules as follows: an angle detecting board, an encoder, and a limit switch. In an example of the present disclosure, the rotating angle of the turntable 220 may be detected by a plurality of detecting sub-modules. When a difference between the detected angles is large, the turntable 220 is controlled to stop moving, so as to implement safety protection for the linear accelerator. For example, the third detecting module includes a second angle detecting board and a third encoder. The controlling module 701 may further be configured to control the turntable 220 to stop moving when a difference between an angle detected by the second angle detecting board and an angle detected by the third encoder reaches a third preset difference value. In an example, the angle detected by the second detecting board and the angle detected by the third encoder may be compared in real time.

In an example, the first detecting module includes any one or more detecting sub-modules as follows: a height detecting board, an encoder, and a limit switch.

According to an example of the present disclosure, the vertical height of the graduated scale on the turntable 220 may be detected by a plurality of detecting sub-modules. When a difference between the detected heights is large, the graduated scale is controlled to stop moving, so as to implement safety protection for the linear accelerator. For example, the first detecting module includes a height detecting board and a first encoder. The controlling module 701 may further be configured to control the graduated scale on the turntable 220 to stop moving when a difference between a height detected by the height detecting board and a height detected by the first encoder reaches a first preset difference value. In an example, the heights detected by the height detecting board and the first encoder may be compared in real time.

In an example of the present disclosure, the limit switches not only is configured to determine whether the gantry 210 and the turntable 220 reach the first preset position and the second preset position, but also is configured to limit maximum motion ranges of the gantry 210 and the turntable 220, so as to avoid that the rotation angles of the gantry 210 and the turntable 220 and the vertical height exceeds respective safety ranges. Detailed description will be made as below.

In an example, a second limit switch is further arranged on the gantry 210. The second limit switch is arranged at a position corresponding to a maximum rotating limit (i.e., maximum rotating motion limit) of the gantry 21, e.g., at a position where the rotating angle is 0 degree, a position where the rotating angle is 180 degrees. The controlling module 701 may be further configured to control the gantry 210 to stop moving when it is detected that the second limit switch is triggered, which indicates that the gantry 210 rotates to a limit.

In an example, a third limit switch is further arranged on the turntable 220. The third limit switch is arranged at a position corresponding to a maximum rotating limit of the turntable 220, e.g., at a position where the rotating angle is 0 degrees, or a position where the rotating angle is 90 degrees. The controlling module 701 may be further configured to control the turntable 220 to stop moving when it is detected that the third limit switch is triggered, which indicates that the turntable 22 has rotated to a limit.

In an example, when a graduated scale is arranged on the turntable 220, the first limit switch is further arranged on the turntable 220, where the first limit switch is arranged at a position corresponding to a maximum vertical limit (including an ascending limit and/or a descending limit) of the graduated scale. The controlling module 701 may be further configured to control the graduated scale to stop moving when it is detected that the first limit switch is triggered, which indicates that the height of the graduated scale has reached the ascending limit or the descending limit.

Detail processing processes about the system, the device and the modules are same as respective processes in examples above, which are not repeatedly described herein.

The methods, processes and modules described herein may be implemented by hardware (including hardware logic circuitry), software or firmware or a combination thereof. The term 'processor' is to be interpreted broadly to include a processing module, ASIC, logic module, or programmable gate array etc. The processes, methods and functional modules may all be performed by the one or more processors; reference in this disclosure or the claims to a 'processor' should thus be interpreted to mean 'one or more processors'.

The figures are only illustrations of an example, wherein the modules or procedure shown in the figures are not necessarily essential for implementing the present disclosure. Those skilled in the art will understand that the modules in the device in the example can be arranged in the device in the examples as described, or can be alternatively located in one or more devices different from that in the examples. The modules in the examples described can be combined into one module or further divided into a plurality of sub-modules.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of controlling a linear accelerator, comprising:

controlling a first component of the linear accelerator to move according to a motion instruction;

when it is detected that the first component reaches a first position, controlling the first component to pause moving and controlling a second component of the linear accelerator to move in a preset direction in a way that the second component moves away from a moving path of the first component;

when it is detected that the second component reaches a second position, controlling the second component to stop moving, and controlling the first component to continue moving according to the motion instruction, wherein the second component reaching the second position indicates that the second component, or a component connected with the second component, moves beyond the moving path of the first component; and controlling a graduated scale on a turntable to stop moving when a difference between a height detected by a height detecting board and a height detected by an encoder reaches a preset difference value, wherein the first component is a gantry of the linear accelerator and the second component is the turntable of the linear accelerator; or the first component is the turntable and the second component is the gantry, the graduated scale is arranged on an upper surface of the turntable and capable of ascending and descending in a vertical direction by being driven through a vertical motor, and the height detecting board and the encoder are configured to detect a vertical height of the graduated scale.

2. The method according to claim 1, wherein when the first component is the gantry and the second component is the turntable, the first component reaching the first position indicates that a rotating angle of the gantry reaches a first preset angle;

the second component reaching the second position in the preset direction indicates that a rotating angle of the turntable reaches a second preset angle.

3. The method according to claim 2, wherein the second component reaching the second position in the preset direction further indicates the vertical height of the graduated scale on the turntable reaches a first preset height.

4. The method according to claim 1, wherein when the first component is the turntable and the second component is the gantry, the first component reaching the first position indicates that a rotating angle of the turntable reaches a third preset angle; and the second component reaching the second position in the preset direction indicates that a rotating angle of the gantry reaches a fourth preset angle.

5. The method according to claim 4, wherein the first component reaching the first position further indicates that the vertical height of the graduated scale on the turntable reaches a second preset height.

6. The method according to claim 1, further comprising:

controlling the gantry to stop moving when a difference between an angle detected by a first angle detecting board and an angle detected by a first encoder reaches a first preset difference value, wherein the first angle detecting board and the first encoder are configured to detect a rotating angle of the gantry.

7. The method according to claim 1, further comprising:

controlling the turntable to stop moving when a difference between an angle detected by a second angle detecting board and an angle detected by a second encoder reaches a second preset difference value, wherein the second angle detecting board and the second encoder are configured to detect a rotating angle of the turntable.

8. A device for controlling a linear accelerator, comprising:

a processor, and a non-transitory machine-readable storage medium storing machine executable instructions which are executable by the processor to:

control a first component of the linear accelerator to move according to a motion instruction;

when it is detected that the first component reaches a first position, control the first component to pause moving and control a second component of the linear accelerator to move in a preset direction in a way that the second component moves away from a moving path of the first component;

when it is detected that the second component reaches a second position, controlling the second component to stop moving and controlling the first component to continue moving according to the motion instruction, wherein the second component reaching the second position indicates that the second component or a component connected with the second component moves beyond the moving path of the first component; and control a graduated scale on a turntable to stop moving when a difference between a height detected by a height detecting board and a height detected by an encoder reaches a preset difference value, wherein the first component is a gantry of the linear accelerator and the second component is the turntable of the linear accelerator; or the first component is the turntable and the second component is the gantry, the graduated scale is arranged on an upper surface of the turntable and capable of ascending and descending in a vertical direction by being driven through a vertical motor, and the height detecting board and the encoder are configured to detect a vertical height of the graduated scale.

9. The device according to claim 8, wherein when the first component is the gantry and the second component is the turntable, the first component reaching the first position indicates that a rotating angle of the gantry reaches a first preset angle;

the second component reaching the second position in the preset direction indicates that a rotating angle of the turntable reaches a second preset angle.

10. The device according to claim 9, wherein the second component reaching the second position in the preset direction further indicates the vertical height of the graduated scale on the turntable reaches a first preset height.

11. The device according to claim 8, wherein when the first component is the turntable and the second component is the gantry, the first component reaching the first position indicates that a rotating angle of the turntable reaches a third preset angle; and the second component reaching the second position in the preset direction indicates that a rotating angle of the gantry reaches a fourth preset angle.

12. The device according to claim 11, wherein
the first component reaching the first position further indicates that the vertical height of the graduated scale on the turntable reaches a second preset height.

13. The device according to claim 8, wherein the instructions are further executable by the processor to:
control the gantry to stop moving when a difference between an angle detected by a first angle detecting board and an angle detected by a first encoder reaches a first preset difference value, wherein
the first angle detecting board and the first encoder are configured to detect a rotating angle of the gantry.

14. The device according to claim 8, wherein the instructions are further executable by the processor to:
control the turntable to stop moving when a difference between an angle detected by a second angle detecting board and an angle detected by a second encoder reaches a second preset difference value, wherein
the second angle detecting board and the second encoder are configured to detect a rotating angle of the turntable.

15. A linear accelerating system, comprising:
a linear accelerator; and
a device for controlling the linear accelerator;
wherein the device for controlling the linear accelerator comprises:
a processor, and
a non-transitory machine-readable storage medium storing machine executable instructions which are executable by the processor to:
control a first component of the linear accelerator to move according to a motion instruction;
when it is detected that the first component reaches a first position, control the first component to pause moving and control a second component of the linear accelerator to move in a preset direction in a way that the second component moves away from a moving path of the first component;
when it is detected that the second component reaches a second position, controlling the second component to stop moving and controlling the first component to continue to move according to the motion instruction, wherein the second component reaching the second position indicates that the second component or a component connected with the second component moves outside the moving path of the first component; and
control a graduated scale on a turntable to stop moving when a difference between a height detected by a height detecting board and a height detected by an encoder reaches a preset difference value,
wherein the first component is a gantry of the linear accelerator and the second component is the turntable of the linear accelerator; or the first component is the turntable and the second component is the gantry,
the graduated scale is arranged on an upper surface of the turntable and capable of ascending and descending in a vertical direction by being driven through a vertical motor, and
the height detecting board and the encoder are configured to detect a vertical height of the graduated scale.

16. The system according to claim 15, wherein when the first component is the gantry and the second component is the turntable,
the first component reaching the first position indicates that a rotating angle of the gantry reaches a first preset angle;
the second component reaching the second position in the preset direction indicates that a rotating angle of the turntable reaches a second preset angle.

17. The system according to claim 16, wherein the second component reaching the second position in the preset direction further indicates the vertical height of the graduated scale on the turntable reaches a first preset height.

18. The system according to claim 15, wherein when the first component is the turntable and the second component is the gantry,
the first component reaching the first position indicates that a rotating angle of the turntable reaches a third preset angle; and
the second component reaching the second position in the preset direction indicates that a rotating angle of the gantry reaches a fourth preset angle.

19. The system according to claim 18, wherein
the first component reaching the first position further indicates that the vertical height of the graduated scale on the turntable reaches a second preset height.

* * * * *